United States Patent
Levant et al.

(10) Patent No.: US 10,274,435 B2
(45) Date of Patent: Apr. 30, 2019

(54) METHOD AND SYSTEM FOR OPTICAL METROLOGY IN PATTERNED STRUCTURES

(71) Applicant: NOVA MEASURING INSTRUMENTS LTD., Rehovot (IL)

(72) Inventors: Boris Levant, Rehovot (IL); Yanir Hainick, Tel-Aviv (IL); Vladimir Machavariani, Rishon LeZion (IL); Roy Koret, Raanana (IL); Gilad Barak, Rehovot (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 15/523,896

(22) PCT Filed: Nov. 2, 2015

(86) PCT No.: PCT/IL2015/051063
§ 371 (c)(1),
(2) Date: May 2, 2017

(87) PCT Pub. No.: WO2016/067296
PCT Pub. Date: May 6, 2016

(65) Prior Publication Data
US 2018/0052119 A1 Feb. 22, 2018

Related U.S. Application Data

(60) Provisional application No. 62/074,041, filed on Nov. 2, 2014.

(51) Int. Cl.
*G01N 21/956* (2006.01)
*G01B 11/02* (2006.01)
*G01N 21/95* (2006.01)

(52) U.S. Cl.
CPC .......... *G01N 21/956* (2013.01); *G01B 11/02* (2013.01); *G01N 21/9501* (2013.01); *G01B 2210/56* (2013.01); *G01N 2201/12* (2013.01)

(58) Field of Classification Search
CPC ............. G01N 21/956; G01N 21/9501; G01N 2201/12; G01B 11/02
See application file for complete search history.

(56) References Cited

U.S. PATENT DOCUMENTS

| | | | | |
|---|---|---|---|---|
| 7,760,368 B2 * | 7/2010 | Finarov | .................. | G01B 11/24 356/614 |
| 8,142,965 B2 * | 3/2012 | Yoel | ..................... | G01B 11/303 356/600 |

(Continued)

*Primary Examiner* — Mohamed Charioui
*Assistant Examiner* — Eyob Hagos
(74) *Attorney, Agent, or Firm* — Alphapatent Associates, Ltd; Daniel J. Swirsky

(57) ABSTRACT

A data analysis method and system are presented for use in determining one or more parameters of a patterned structure located on top of an underneath layered structure. According to this technique, input data is provided which includes first measured data PMD being a function $f$ of spectral intensity $I\lambda$ and phase $\varphi$, $PMD=f(I_\lambda;\varphi)$, corresponding to a complex spectral response of the underneath layered structure, and second measured data $S_{meas}$ indicative of specular reflection spectral response of a sample formed by the patterned structure and the underneath layered structure. Also provided is a general function F describing a relation between a theoretical optical response $S_{theor}$ of the sample and a modeled optical response $S_{model}$ of the patterned structure and the complex spectral response PMD of the underneath layered structure, such that $S_{theor}=F(S_{model}; PMD)$. The general function is then utilized for comparing the second measured data $S_{meas}$ and the theoretical optical response $S_{theor}$, and determining parameter(s) of interest of the top structure.

15 Claims, 4 Drawing Sheets

(56) References Cited

U.S. PATENT DOCUMENTS

| | | |
|---|---|---|
| 8,798,966 B1 | 8/2014 | Hench et al. |
| 2005/0062965 A1* | 3/2005 | Scheiner ............... G01B 11/02 356/319 |
| 2008/0062406 A1* | 3/2008 | Finarov ................. G01B 11/24 356/73 |
| 2013/0124141 A1* | 5/2013 | Brill .................. G01B 11/0625 702/155 |
| 2016/0266036 A1* | 9/2016 | Freese ................... G01N 21/51 |

* cited by examiner

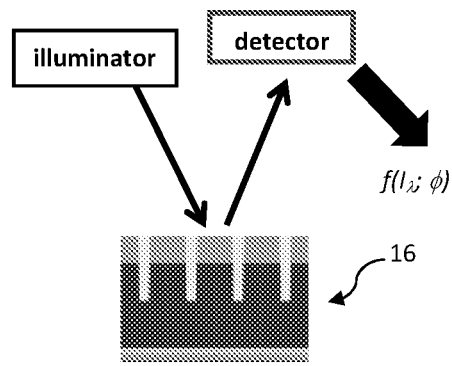
FIG. 5
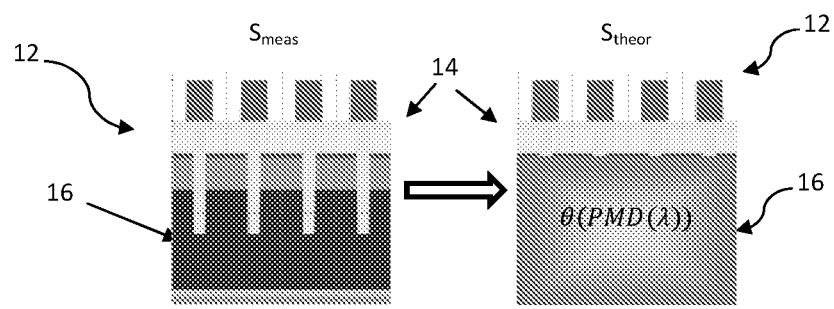
FIG. 6
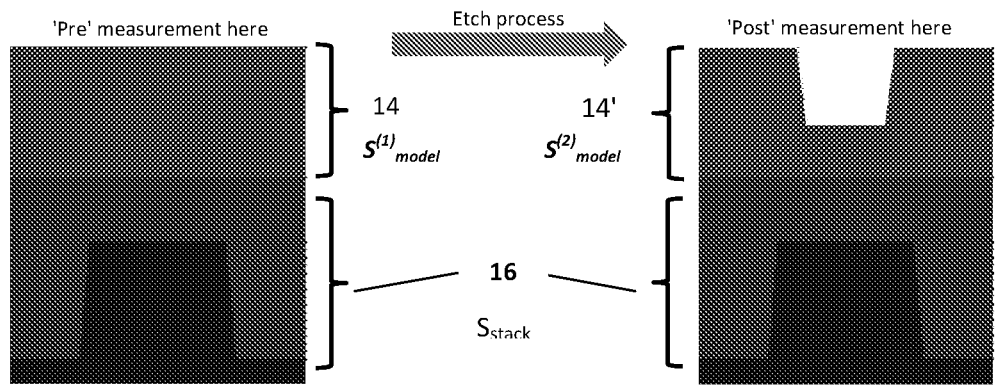
Fig. 7A
Fig. 7B

METHOD AND SYSTEM FOR OPTICAL METROLOGY IN PATTERNED STRUCTURES

TECHNOLOGICAL FIELD

The present invention is generally in the field of optical inspection/measurement of patterned structures, and relates to a method and system for Optical Critical Dimension (OCD) metrology, particularly useful for measurements on semiconductor wafers.

BACKGROUND

As semiconductor technology progresses, microelectronic devices are being fabricated by ever-shrinking dimensions. This development dictates the necessity to employ accurate and reliable metrology, which becomes an increasingly complex and important task. Complementing measurement channels and modeling techniques, allowing the required improvements in measurement capabilities, are essential for the continual process of this development.

Commonly, Optical Critical Dimension (OCD) metrology plays an important role in semiconductor manufacturing process control, due to its unique advantages: it is sensitive, accurate, flexible and relatively fast. OCD metrology is applied to acquire highly accurate and precise information on the geometry and material properties of these structures.

In OCD, measured data including optical scattering information is collected, and analyzed/interpreted using theoretical model(s). The data analysis includes modification of the geometrical and material properties in the modeled structure until a combination of the parameters is found which corresponds to a good agreement between the theoretical (calculated) and measured data. It is then assumed that the model parameters (dimensions, thicknesses, material optical properties etc.), which were found to provide good agreement (best fit) with the measurement, represent the parameters of the measured structure.

GENERAL DESCRIPTION

There is a need in the art for a novel approach for OCD metrology, especially for inspecting/measuring in patterned structures in the form of different sub-structures stacked on one another. This is associated with the following:

One of the main challenges in modern OCD is the calculated overhead, required to predict the spectral response from the measured structure, a procedure which is highly non-trivial. In many cases, metrology is used to identify attributes located in a well-defined area of a patterned structure (microelectronic structure). Such case, for example, is common in post-CMP and post-CVD stages of the manufacturing process, where the goal of metrology is to characterize geometrical parameters or features in the top layers of a structure located on an underneath stack. However, light, which is incident on the top surface of the structure, penetrates into the structure, and interacts with layers below the region of interest.

In this connection, reference is made to FIG. 1, schematically illustrating a structure 10 in the form of a stack of sub-structures 10A, 10B and 10C (each being a single- or multi-layer structure). The structure 10 is configured such that top sub-structure 10A includes layer(s) with parameters of interest, intermediate sub-structure 10B includes layer(s) without parameter(s) of interest but which are affected from significant interaction with the incoming signal, and a bottom sub-structure 10C includes underlayer(s) that do not experience any interaction with incoming light.

As a result, a complete description of the geometry and materials is necessary in order to model a light response of the structure 10 (e.g. light returned from the structure in response to illumination), both for the layer(s) of interest and underlayer(s). Nevertheless, deeper layers experiencing almost zero interaction with the incoming signal can be disregarded in the modeling process.

However, continuous shrinkage in the dimensions of electronic devices, top layers become more transparent, and accordingly increasingly deeper layers have to be considered in the model of an optical response of the entire structure. The resulting challenge stems from the requirement to take into account the underlayers. Underlayers, either being patterned or not, may be complex, resulting with increased modeling challenge. Even worse, these underlayers may be unknown, rendering the modeling side of the OCD metrology bargain almost impossible. Moreover, underlayers may differ between different vendors, lots, wafers, and even within the same wafer. Solving each case separately is unfeasible and impractical.

Overcoming these challenges is of high importance today, and is expected to grow more and more important. The approach of the present invention is based on a new methodology which the inventors call Selective Modeling (SM), which enables disregarding the underlayer modeling problem.

The basic concept of the invention is aimed at treating layers with no parameters of interest to metrology, but with burdening contribution to the modeling and calculation overhead due to significant coupling to the rest of the layers. The invention utilizes preliminary measurement on these layers and using data indicative of a complex spectral response of these layers for accurate but simple description of the optical response from the entire structure.

Thus, according to one broad aspect of the invention, it provides a data analysis method for use in determining one or more parameters of a patterned structure located on top of an underneath layered structure. The data analysis method is carried out by a computer system and comprises:

providing input data which comprises first measured data PMD being a function $f$ of spectral intensity $I_\lambda$ and phase $\phi$, $PMD=f(I_\lambda; \phi)$, corresponding to a complex spectral response of the underneath layered structure, and second measured data $S_{meas}$ indicative of specular reflection spectral response of a sample formed by said patterned structure and the underneath layered structure;

providing a general function F describing a relation between a theoretical optical response $S_{theor}$ of the sample formed by the patterned structure and the underneath layered structure and a modeled optical response $S_{model}$ of the patterned structure and the complex spectral response PMD of the underneath layered structure, such that $S_{theor}=F(S_{model}; PMD)$; and utilizing the general function $F(S_{model}; PMD)$ and comparing the second measured data $S_{meas}$ and the theoretical optical response $S_{theor}$, and determining one or more parameters of the structure corresponding to a best fit condition between the second measured data and the theoretical optical response.

As indicated above, the underneath structure may or may not be patterned. As also indicated above, the top and bottom structures may directly interface with one another or via intermediate layer(s).

The general function F actually defines a relation between the theoretical (modeled) response $S_{theor}$ of the entire sample at one side and the contribution of each of the top and bottom structures to this response. This approach is based on the inventors' understanding that the measured spectral response from the entire sample $S_{meas}$ is formed by the spectral response of the top structure $S_{top}$ (structure of interest), and a spectral response caused by light interaction with the bottom structure. This interaction related response $S_{inter}$ in turn depends on the complex spectral response of the bottom structure, i.e. $S_{inter}$(PMD). Thus, the function F presents a relation between $S_{theor}$ (which is function of $S_{model}$ and PMD) and $S_{meas}$ which is a function of $S_{top}$ and $S_{inter}$. For example, the total spectral intensity $(I(\lambda))_{total}$ of the optical response of the entire sample $S_{meas}$ may be a function of the spectral intensity in the top structure response $(I(\lambda))_{top}$ and of the sum of $(I(\lambda))_{top}$ and PMD.

The first measured data PMD=$f(I_\lambda; q)$ about the underneath layered structure is obtained by carrying out a preliminary measurement session on the underneath structure. In some embodiments, the preliminary measurement session may direct provide both the spectral intensity $I\lambda$ and phase $\phi$ data. This may for example be achieved by using an interferometric measurement. In some other embodiments, the preliminary measurement session provides direct measurement of the spectral intensity $I_\lambda$, and the phase $\phi$ data is then reconstructed, e.g. by using measurements with different polarization alignments, or by using modeling of the spectral reflectivity of the underneath structure, or by applying a complex-functions processing to the reflectivity data.

According to another aspect of the invention, there is provided a measurement system for determining one or more parameters of a patterned structure located on top of an underneath layered structure. The measurement system comprises a computer system comprising:

data input utility for receiving input data comprising first measured data PMD indicative of spectral intensity $I_\lambda$ and phase $\phi$, PMD=$f(I_\lambda; \phi)$, corresponding to a complex spectral response of the underneath layered structure, and second measured data $S_{meas}$ indicative of specular reflection spectral response of a sample formed by said patterned structure and the underneath layered structure; and data processor utility connected to the data input utility for receiving and processing the first and second measured data, the data processing utility comprising:

a general function generator that generates a function F describing a relation between a theoretical optical response $S_{theor}$ of the sample formed by the patterned structure located on top of the underneath layered structure, and a modeled optical response $S_{model}$ of the patterned structure and the complex spectral response PMD of the underneath layered structure, such that $S_{theor}$=F($S_{model}$; PMD); and an analyzer module preprogrammed for utilizing said general function and comparing the second measured data $S_{meas}$ and the theoretical optical response $S_{theor}$, and determining one or more parameters of the structure corresponding to a best fit condition between the second measured data and the theoretical optical response.

The system may further comprise a communication utility for connecting to an external device and receiving data indicative of the first and second measured data. Such external device may be a measurement unit (on line mode of data analysis) or a storage device (off line mode of data analysis).

The external device may provide the first measured data comprising the spectral intensity $I_\lambda$ and phase $\phi$ of the underneath structure; or may provide the first measured data comprising only the spectral intensity $I_\lambda$ response of the underneath structure, in which case the data processor utility further comprises an extractor module for extracting the phase $\phi$ data from the spectral intensity $I_\lambda$ response.

The measurement unit may be configured for performing an interferometric measurement scheme (spectral interferometer) and/or for performing measurements with different polarization alignments (polarized spectral reflectometry (SR) or spectral ellipsometry (ER), etc.).

According to yet another aspect of the invention, it provides a data analysis program storage device readable by machine, tangibly embodying a program of instructions executable by the machine to perform a method for use in determining one or more parameters of a patterned structure located on top of an underneath layered structure, the method being carried out by a computer system and comprising:

providing input data which comprises first measured data PMD being a function $f$ of spectral intensity $I_\lambda$ and phase $\phi$, PMD=$f(I_\lambda; \phi)$, corresponding to a complex spectral response of the underneath layered structure, and second measured data $S_{meas}$ indicative of specular reflection spectral response of a sample formed by said patterned structure and the underneath layered structure; and providing a general function F describing a relation between a theoretical optical response $S_{theor}$ of the sample formed by the patterned structure and the underneath layered structure and a modeled optical response $S_{model}$ of the patterned structure and the complex spectral response PMD of the underneath layered structure, such that $S_{theor}$=F($S_{model}$; PMD);

utilizing said general function F($S_{model}$; PMD) and comparing the second measured data $S_{meas}$ and the theoretical optical response $S_{theor}$, and determining one or more parameters of the structure corresponding to a best fit condition between the second measured data and the theoretical optical response.

According to yet another aspect of the invention, there is provided a data analysis computer program product comprising a computer useable medium having computer readable program code embodied therein for use in determining one or more parameters of a patterned structure located on top of an underneath layered structure, the computer program product comprising:

computer readable program code for causing the computer to provide input data which comprises first measured data PMD being a function $f$ of spectral intensity $I_\lambda$ and phase $\phi$, PMD=$f(I_\lambda;\phi)$, corresponding to a complex spectral response of the underneath layered structure, and second measured data $S_{meas}$ indicative of specular reflection spectral response of a sample formed by said patterned structure and the underneath layered structure; and computer readable program code for causing the computer to provide a general function F describing a relation between a theoretical optical response $S_{theor}$ of the sample formed by the patterned structure and the underneath layered structure and a modeled optical response $S_{model}$ of the patterned structure and the complex spectral response PMD of the underneath layered structure, such that $S_{theor}$=F ($S_{model}$; PMD);

computer readable program code for causing the computer to utilize said general function F($S_{model}$; PMD) and comparing the second measured data $S_{meas}$ and the theoretical optical response $S_{theor}$, and determining one or more parameters of the structure corresponding to a best fit condition between the second measured data and the theoretical optical response.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIG. 5 schematically illustrates the stage of preliminary measurements on the underneath stack, according to the method of the invention;

FIG. 6 schematically illustrates the principles of the invention regarding replacement of the spectral response data of the underneath stack in a modeled spectral response of the entire sample by an effective model of the spectral response of the underneath stack; and FIGS. 7A and 7B exemplify the creation of the effective model of the spectral response of the underneath stack, by using etch process, showing respectively 'pre' and 'post' measurements on the sample prior to and after the Etch process.

DETAILED DESCRIPTION OF EMBODIMENTS

Figure 1:
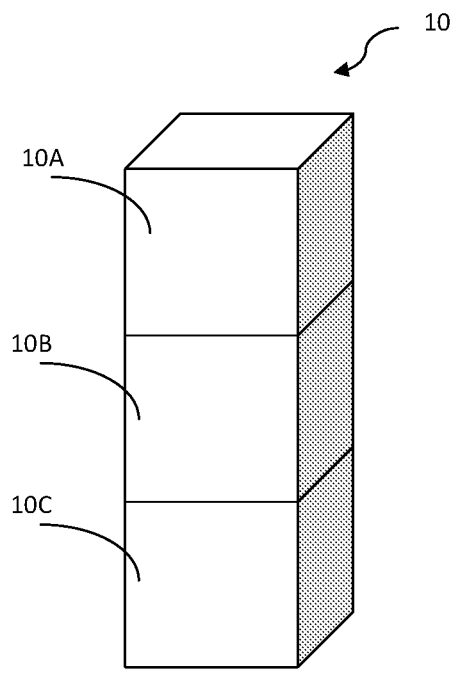
FIG. 1 schematically illustrates a patterned structure in the form of a stack of sub-structures, which are different from one another with respect to pattern parameters of interest and optical response to incoming light.

The present invention provides for a novel approach, termed here Selective Modeling (SM), for modeling an optical response of a multi-layer structure, e.g. structure 10 of FIG. 1, including top layers with parameters of interest located above underlayer(s) with no parameters of interest.

Figure 2:
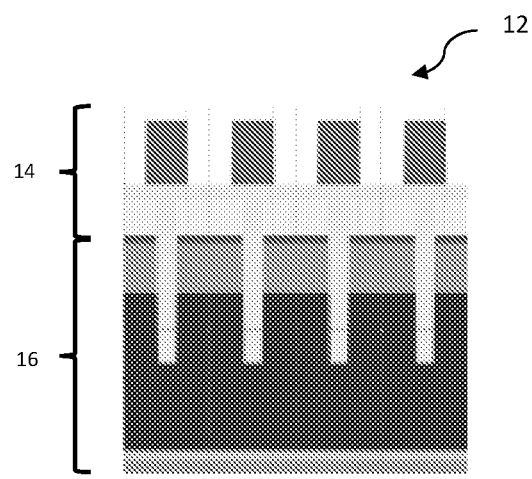
FIG. 2 illustrates an example of a sample of the type to be measured using the technique of the invention, being in the form of a top patterned structure containing parameters of interest (structure to be measured) located above an underneath stack.

Reference is made to FIG. 2 illustrating a sample 12 in the form of a top structure/stack (upperlayers) 14 containing parameters of interest, located above a bottom structure/underneath stack (underlayers) 16 with no parameters of interest. It should be noted that the top structure of interest 14 is located above the underneath stack 16, meaning that structure 14 may be placed directly on top of the underneath stack 16 or via an intermediate/interfacing layer(s). The top structure 14 is typically a patterned structure, and may have patterns of features with small dimensions (both in horizontal and vertical planes), while the underneath stack 16 may or may not be a patterned structure.

Light incident on the top structure 14 can penetrate down to the underlayers 16, so that a measured radiation (e.g. optical) response of the entire sample 12 is indicative of the optical properties of the underlayers 16. Hence, the top structure 14 that is to be measured, i.e. including parameters of interest, is located above the bottom structure 16, which, while not being of interest (not to be measured), affects an optical response from the entire sample 12.

Typically, the configuration of the underneath stack 16 is not known a priori, and therefore the optical response of the entire sample 12 is hard (if not impossible) to model. Generally, preliminary measurements of the parameters of the underneath stack 16 might be used for optimizing an optical model describing the optical response of the entire structure 12. However, this approach is not suitable in most cases, because in most cases the underneath stack 16 is complex, includes patterned layer(s), and also may be different from structure to structure thus each time requiring remodeling of the optical response of the underneath stack.

The present invention provides a novel measurement technique for measuring on a structure of the type located above an underneath stack (layers). The technique of the invention avoids a need for modeling the optical response of the underneath stack as well as avoids a need for calculation of the parameters of the underneath stack for optimization of the total optical model. The invention utilizes preliminary measurement of an optical complex spectral response of the underneath stack for accurate and simple description of the optical response from the entire sample 12. To this end, the invention utilizes a predefined function describing a relation between theoretical (modeled) optical response of the entire sample 12, and the complex spectral response of the underneath stack and a modeled optical response of the upperlayers 14 (structure to be measured).

Figure 3:
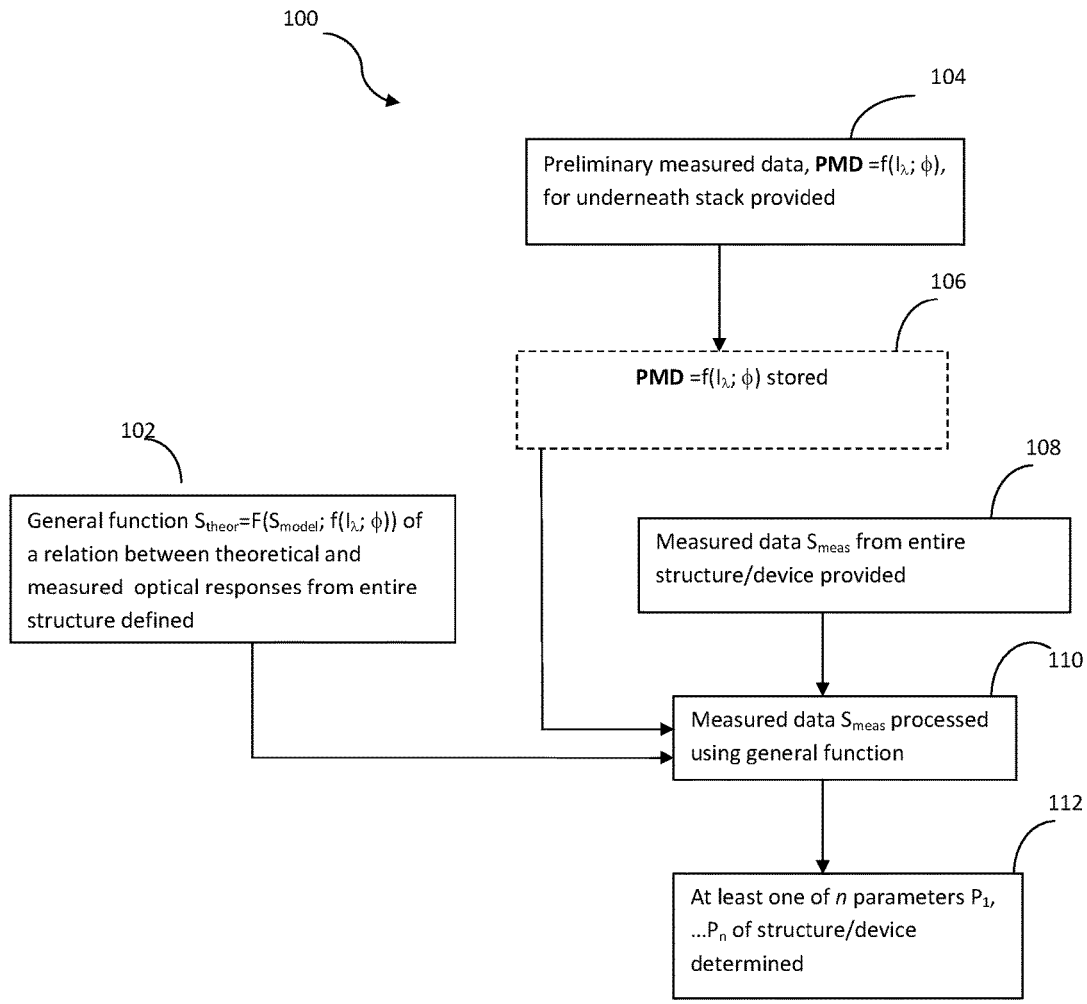
FIG. 3 illustrates a flow diagram of the method of the invention.

Reference is made to FIG. 3 illustrating a flow diagram 100 of the method of the invention. As shown, a general function F is provided/defined (step 102), describing a relation between theoretical optical response $S_{theor}$ of the entire sample 12, a modeled optical response $S_{model}$ of the top structure 14, and a complex spectral response of the underneath stack 16 being a function $f$ of spectral intensity $I_\lambda$ and phase $\phi$ data, i.e. $S_{theor}=F(S_{model}; f(I_\lambda; \phi))$. The modeled optical response $S_{model}$ of the upperlayers 14 is typically a function of n parameters $P_1, \ldots, P_n$ of the upperlayers 14.

To this end, preliminary measured data (first measured data) PMD from the underneath stack 16 (generally, at least a portion/site thereof) is provided (step 104). This preliminary measured data is indicative of a complex spectrum of the underneath stack 16, i.e. $PMD=f(I_\lambda; \phi)$. This preliminary measured may be stored (step 106).

As indicated above, such preliminary measured data PMD may be obtained from an optical measurement unit (on line mode) or from an external storage device (off line mode). As will be described below, the spectral intensity $I_\lambda$ and phase $\phi$ data may be directly and concurrently determined from the preliminary measurements, or the case may be such that the spectral intensity $I_\lambda$ is directly measured while the phase $\phi$ data is separately extracted (e.g. using modeling or causality relations).

Total measured spectrum (second measured data), $S_{meas}$, from the entire sample 12 is provided (step 108), and processed (step 110). The processing is performed using the previously defined general function F describing the relation between modeled/theoretical optical response $S_{theor}$ of the entire sample 12 and the modeled response $S_{model}$ of the top structure and complex spectral response $f(I_\lambda; \phi)$ of the underneath stack, and fitting procedure between the theoretical and measured data. This enables determination of one or more parameters of the upperlayers 14 (step 112).

Figure 4:
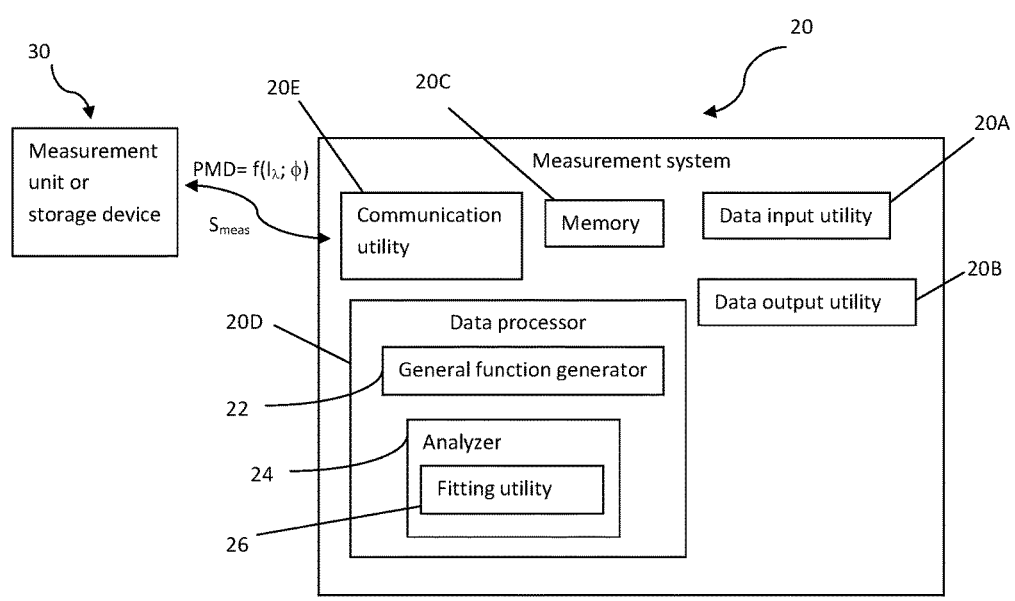
FIG. 4 is a block diagram of a measurement system of the invention.

FIG. 4 schematically illustrates a data analysis system 20 of the present invention for implementing the above method. The data analysis system 20 includes a computer system including inter alia data input and output utilities 20A, 20B, memory 20C, and processor utility 20D. The system 20 also includes a suitable communication utility 20E for data communication (via wires or wireless signal transmission) with an external device 30 for receiving measured data. Such external device 30 may be an optical measurement unit itself or a stand alone storage device.

The data processor utility 20D includes a general function generator 22 configured for generating the above-described function F based on a selected model for modeling the optical response $S_{model}$ for a structure under measurements. As indicated above, the modeled optical response $S_{model}$ of the upper stack 14 is a function of n parameters of the upper stack 14. There is a variety of known models describing a relation between parameters of a pattern structure and an optical response of such structure, for a given measurement scheme.

The processor 20D also includes an analyzer module 24 including a fitting module 26. The analyzer 24 is preprogrammed for utilizing the general function/relation $S_{theor}=F(S_{model}; f(I_\lambda; \phi))$ and comparing the total measured data $S_{meas}$ and the theoretical data $S_{theor}$, while modifying the parameters in the theoretical data, and upon achieving the best fit (according to predetermined tolerances/thresholds) with the measured data determining the corresponding one or more parameters of the structure 14.

The optical measurement unit 30 may be of any known suitable configuration for applying broadband illumination to a structure/sample and detecting a spectral response of the structure (being function of spectral intensity and phase). To this end, the measurement unit includes a spectrophotometric detector, and may include an interferometric module and/or polarization affecting assembly in order to determine both the amplitude and phase of the measured signal. The configuration and operation of the measurement unit do not form part of the invention and therefore need not be specifically described, except to note the following: The optical response from a patterned structure is actually in the form of a diffraction pattern. The inventors have found that for illuminating wavelengths (wavelength range) λ larger than the period(s) of pattern(s) in the structure 12 under measurements (which is typically the case at least for such patterned structures as semiconductor wafers of current technology nodes), mainly light components corresponding to zero order diffraction of the underneath stack 16 interact with the upperlayers 14 and thus affect the detectable optical response of the entire sample 12. The measurement scheme for spectrophotometric measurements includes detection of zero-order spectral response from the structure. Thus, measured data (the preliminary measured PMD from the underneath stack 16 and the total measured data MD from the entire sample 12), is indicative of the zero-order spectral response of the respective structure.

The preliminary measurements on the underneath stack 16 could be performed on the stack 16 prior to manufacturing the upper stack 14 on top thereof, or on a portion of the underneath stack 16, i.e. a measurement site on stack 16, without the upper stack 14.

Thus, the invention utilizes gaining knowledge of the spectral complex reflectivity (both amplitude and phase) of the underlayers' stack 16 and defining a general function describing a relation between the theoretical response of the sample, modeled response of the top structure, and the complex spectral complex reflectivity of the underneath stack.

It should be understood, that according to the invention, the complex reflectance of the underneath stack is translated to a valid model of optical response: $PMD(\lambda)=r(\lambda)e^{i\phi(\lambda)}$, with $r(\lambda)$ the reflected amplitude and $\phi(\lambda)$ the spectral phase, without a need for calculation of the parameters of the underneath stack. The above described general function F actually presents some kind of an effective model describing the reflected electromagnetic field (at each wavelength) that would result from the interaction between light shone on the underlayer, and the underlayer's structure (stack). The spectral reflectivity, namely the amplitude-dependent reflected intensity, is given by $I=|r(\lambda)|^2$. Obtaining the complex reflectivity can be done in several ways, as will be described further below. However, in any case this requires preliminary measurement of the underneath structure 16 before the growth (manufacturing) of the upperlayers 14.

Reference is made to FIG. 5 schematically illustrating such preliminary measurements on the underneath stack 16. As shown, the stack 16 is illuminated by broadband light and specular reflection (zero-order response) for each wavelength is detected, providing preliminary complex spectral measured data $PMD=f(I_\lambda; \phi)$. The so-acquired spectral information is used to represent the effect/contribution of the optical response of the underneath stack 16, $\theta(PMD(\lambda))$ on the total optical response of the sample.

The modeling of the optical response of the upperlayer structure 14 can be performed in any known suitable way for a patterned structure characterized by n parameters. The upperlayer spectral response model $S_{model}$ and the effect of the underneath stack $\theta(PMD(\lambda))$ are combined into a complete effective model $S_{theor}$ of the spectral response of the sample 12, according to the predetermined function $S_{theor}=F(S_{model}; \theta(PMD(\lambda)))$. This is schematically illustrated in FIG. 6 in a self-explanatory manner. Then, standard OCD interpretation scheme can be applied to the total measured data $S_{meas}$ from the sample 12, using the general function F.

It may be the case that a measurement of the underneath stack 16 cannot be taken directly below the upperlayers 14. In that case, a measurement of a previous process step (which samples also the underlayer under consideration) may also be used for the Selective Modeling method.

For instance, let us consider an Etch process step with the available measurements. This is schematically illustrated in FIGS. 7A and 7B, showing respectively 'pre' and 'post' measurements on the sample 12 prior to and after the Etch process. It should be noted that these two measurements are performed with the same underlayers' structure 16 characterized by the same complex spectral response, and different configurations of the upperlayers' structures 14 and 14'. In this case, by taking into account the two upperlayers' models $S^{(1)}$ model and $S^{(2)}$ model for the 'pre' application and 'post' application respectively, the complex spectral response of the underneath stack can be extracted in a similar manner to the above-described technique. The complex spectral response from the underneath stack could be calculated from the first (preliminary) measurement which takes into account a solid (non-patterned) layer on top if the underneath stack.

The following are some specific non-limiting examples of the embodiments of the invention.

The measurement of the complex spectral response of the underneath stack 16 may be implemented using several known techniques. For example, both the spectral reflectivity and spectral can be directly measured. To this end, interferometric measurement schemes can be used which allow direct probe of both the spectral reflectivity and spectral phase of light returned from an illuminated region in the structure. This additional information on the underlayers' stack can greatly stabilize and generalize the applicability of this method.

According to some other examples, only the spectral reflectivity can be measured, and the spectral phase of the underlayer can be then extracted separately. This can be done via calculation and/or modeling. Indeed, it is common for OCD measurements that the measured reflectivity can be used to deduce the measured structure geometry and material properties. Then, the reflected spectral phase from the found structure can be deduced from the simplified model. Alternatively or additionally, the spectral phase of the underlayer can be extracted by causality relations. Since the spectral reflectivity and spectral phase comprise together a complex function (the electric field), in some cases it may be possible to use complex-functions methods (e.g. Kramers-Kronig relations) to extract the phase from the reflectivity.

In yet further examples, the underlayers' reflectivity can be measured with different polarization alignments. In standard-OCD, characterizing the underlayers' effective model can benefit from measuring several independent information channels, specifically the TE/TM polarization measurements. Moreover, the phase reconstruction can greatly benefit from several dependent polarized measurements. For example, TE and TM polarizations are measured and their phases are reconstructed. Then, a third measurement is taken, which mixes polarizations (e.g. at 45° polarization). The phase of the third measurement is directly related to the individual phases of the two first measurements. Such cross-referencing can greatly stabilize the reconstruction.

Also, multiple-angle measurement of the underlayers' reflectivity can be used to better model the required effective layer in case of high order reflections. In a case of non-negligible or even important high-order reflections (the term "high-order" refers to any greater-than-zero-order reflection), measurements of the underlayers' response in angles that differ from the specular, zero-order, reflection can assist in characterizing both the amount of deviation from a simple zero-order reflection, and the needed corrections for the effective model to account for these reflections.

The amount of underlayers to be measured can also be appropriately selected. For example, measurement of the underlayers is performed on each site that is needed for later upperlayer metrology. In fact, it may be the case that variations across the wafer and between wafers, together with high sensitivity to the specific characteristics of the underlayer(s) specific characteristics, require the measurement of the underlayer at each site of interest. In some other examples, measurement of underlayers can be performed on a subset of sites, on each wafer. This is because in cases of low sensitivity to underlayers, small across wafer variations of underlayers or both, a sample of underlayer measurements out of the total sites may be sufficient. In yet further example, underlayers can be measured on solution setup (in controlled, designed experiments), for identification of a few options for effective underlayers. To this end, a 'library' of underlayer properties could be prepared for designed experiments, allowing for the inclusion of the underlayer (in its simple, effective form) in the interpretation process, rather than fixing it.

It should also be noted that underlayer(s) can be measured with reduced accuracy in the case that high quality is not necessarily required. Indeed, if sensitivity to the underlayer is very small, e.g. when there is very low coupling of underlayer to the rest of the structure, even the effective model could be approximate, and high accuracy in reconstructing the effective model's parameters (the spectral phase, for example) may not be crucial.

Further, underlayer-agnostic for part of the spectrum can be used, in the case that an adequate effective model is found for some spectral range but not for other. More specifically, different wavelengths interact in a different way with the sample. Specifically, the sensitivity to the specific attributes of underlayer for parts of the spectrum could be large, and may render the solution impossible. Nevertheless, since different wavelengths are generally completely decoupled, the underlayer-agnostic solution could be implemented to the parts of the spectrum where it is valid, and not for the rest.

Thus, the present invention provides an effective and simple solution for accurate measurements in a patterned structure located above an "unknown" structure (stack). The technique of the invention utilizes a predetermined function/relation between the modeled spectral response from the entire sample, and a modeled spectral response of the patterned structure and complex spectral response of the underneath stack (e.g. by direct measurement of both spectral reflectivity and spectral phase, or direct measurement of spectral reflectivity and extraction of phase data).

The technique of the present invention is not limited to any measurement scheme, but may utilize any known suitable measurement scheme for detecting zero-order spectral response from the entire sample, as well as any known suitable measurement scheme for determination of a complex spectral response of the structure.

The invention claimed is:

1. An optical metrology method for use in determining one or more parameters of a patterned structure located on a semiconductor wafer on top of an underneath layered structure on the semiconductor wafer, the method being carried out by a computer system comprising a processor and a memory, the method comprising:
    obtaining first measured data PMD being a function $f$ of spectral intensity $I_\lambda$ and phase $\phi$, PMD=$f(I_\lambda;\phi)$, corresponding to a complex spectral response of the underneath layered structure to incident radiation;
    performing optical measurements of the patterned structure when disposed above the underneath layered structure on the semiconductor wafer, thereby obtaining second measured data $S_{meas}$ indicative of specular reflection spectral response to incident radiation from a sample formed by the patterned structure and the underneath layered structure; and
    determining measurements of physical characteristics of the patterned structure by analyzing, via the processor, the second measured data $S_{meas}$ to determine values for one or more parameters of the structure, wherein the parameters represent the physical characteristics of the structure, the analyzing comprising:
        providing a general function F describing a relation between a theoretical optical response $S_{theor}$ of the sample formed by the patterned structure and the underneath layered structure, a modeled optical response $S_{model}$ of the patterned structure, and the complex spectral response PMD of the underneath layered structure, such that $S_{theor}=F(S_{model};PMD)$, and
        utilizing, via the processor, the general function $F(S_{model};PMD)$ for comparing the second measured data $S_{meas}$ and the theoretical optical response $S_{theor}$ in a fitting procedure, and determining the one or more parameters of the patterned structure from the theoretical optical response $S_{theor}$ corresponding to a best fit condition between the second measured data and the theoretical optical response.

2. The method of claim 1, comprising performing a preliminary measurement session on the underneath layered structure and providing to the processor the first measured data PMD=$f(I_\lambda;\phi)$ about the underneath layered structure prior to manufacturing the patterned structure on the semiconductor wafer.

3. The method of claim 2, wherein the preliminary measurement session directly provides both the spectral intensity $I_\lambda$ and the phase $\phi$ data.

4. The method of claim 3, wherein the preliminary measurement session comprises an interferometric measurement.

5. The method of claim 2, wherein the preliminary measurement session provides direct measurement of the spectral intensity $I_\lambda$, and provides for reconstructing the phase $\phi$ data.

6. The method of claim 5, the preliminary measurement session comprises measurements with different polarization alignments for reconstructing the spectral phase $\phi$ data.

7. The method of claim 5, wherein the phase is reconstructed using modeling spectral reflectivity of the underneath layered structure.

8. The method of claim 5, wherein the spectral phase $\phi$ data is extracted from the reflectivity data by using a complex-functions processing of the reflectivity data.

9. An optical metrology system for determining one or more parameters of a patterned structure located on a semiconductor wafer on top of an underneath layered structure on the semiconductor wafer, wherein the parameters represent physical characteristics of the patterned structure, the measurement system comprising a computer system comprising:
apparatus configured to
obtain first measured data PMD indicative of spectral intensity $I_\lambda$ and phase $\phi$, PMD=$f(I_\lambda;\phi)$, corresponding to a complex spectral response of the underneath layered structure, and
perform optical measurements of the patterned structure when disposed above the underneath layered structure on the semiconductor wafer, thereby obtaining second measured data $S_{meas}$ indicative of specular reflection spectral response of a sample formed by the patterned structure and the underneath layered structure; and
a data processor configured and operable to process the first and second measured data, the data processor configured and operable to execute:
a general function generator that generates a function F describing a relation between a theoretical optical response $S_{theor}$ of the sample formed by the patterned structure located on top of the underneath layered structure, and a modeled optical response $S_{model}$ of the patterned structure and the complex spectral response PMD of the underneath layered structure, such that $S_{theor}=f(S_{model};PMD)$; and
an analyzer module preprogrammed for determining measurements of the physical characteristics of the patterned structure by utilizing the general function and comparing the second measured data $S_{meas}$ and the theoretical optical response $S_{theor}$ in a fitting procedure, and determining values for one or more parameters of the patterned structure from the theoretical optical response $S_{theor}$ corresponding to a best fit condition between the second measured data and the theoretical optical response.

10. The system of claim 9, wherein the first measured data comprises the spectral intensity $I_\lambda$ and phase $\phi$ of the underneath layered structure.

11. The system of claim 9, wherein the first measured data comprises the spectral intensity $I_\lambda$ response of the underneath layered structure, and wherein the data processor comprises an extractor module for reconstructing the phase $\phi$ data from the spectral intensity $I_\lambda$ response.

12. The system of claim 9, wherein the apparatus is a measurement unit configured for performing an interferometric measurement scheme.

13. The system of claim 9, wherein the apparatus is a measurement unit configured for performing measurements with different polarization alignments.

14. A program storage device readable by machine, tangibly embodying a program of instructions executable by the machine to perform an optical metrology method for use in determining one or more parameters of a patterned structure located on a semiconductor wafer on top of an underneath layered structure on the semiconductor wafer, the method being carried out by a computer system, the computer system comprising a processor and a non-transitory memory, and the method comprising:
input data which comprises
obtaining first measured data PMD being a function $f$ of spectral intensity $I_\lambda$ and phase $\phi$, PMD=$f(I_\lambda;\phi)$, corresponding to a complex spectral response of the underneath layered structure to incident radiation;
performing optical measurements of the patterned structure when disposed above the underneath layered structure on the semiconductor wafer, thereby obtaining second measured data $S_{meas}$ indicative of specular reflection spectral response to incident radiation from a sample formed by the patterned structure and the underneath layered structure; and
determining measurements of physical characteristics of the patterned structure by analyzing, via the processor, the second measured data $S_{meas}$ to determine values for one or more parameters of the patterned structure, wherein the parameters represent the physical characteristics of the patterned structure, the analyzing comprising:
providing, via the processor, a general function F describing a relation between a theoretical optical response $S_{theor}$ of the sample formed by the patterned structure and the underneath layered structure, a modeled optical response $S_{model}$ of the patterned structure, and the complex spectral response PMD of the underneath layered structure, such that $S_{theor}$=F($S_{model}$; PMD); and
utilizing, via the processor, the general function F($S_{model}$;PMD) for comparing the second measured data $S_{meas}$ and the theoretical optical response $S_{theor}$ in a fitting procedure, and determining the one or more parameters of the patterned structure from the theoretical optical response $S_{theor}$ corresponding to a best fit condition between the second measured data and the theoretical optical response.

15. A computer program product comprising computer readable program code embodied in a non-transitory computer readable medium, for use in determining one or more parameters of a patterned structure located on a semiconductor wafer on top of an underneath layered structure on the semiconductor wafer, wherein the parameters represent physical characteristics of the structure, the computer program product comprising:
computer readable program code for causing apparatus to
obtain first measured data PMD being a function $f$ of spectral intensity $I_\lambda$ and phase $\phi$, PMD=$f(I_\lambda;\phi)$, corresponding to a complex spectral response of the underneath layered structure to incident radiation, and
perform optical measurements of the patterned structure when disposed above the underneath layered structure on the semiconductor wafer, thereby obtaining second measured data $S_{meas}$ indicative of specular reflection spectral response to incident radiation from a sample formed by the patterned structure and the underneath layered structure;

computer readable program code for causing the computer to determine measurements of the physical characteristics of the patterned structure by analyzing the second measured data $S_{meas}$ to determine values for one or more parameters of the patterned structure, the analyzing comprising: providing a general function F describing a relation between a theoretical optical response $S_{theor}$ of the sample formed by the patterned structure and the underneath layered structure, a modeled optical response $S_{model}$ of the patterned structure, and the complex spectral response PMD of the underneath layered structure, such that $S_{theor}=F(S_{model}; PMD)$; and computer readable program code for causing the computer to utilize the general function $F(S_{model}; PMD)$ and comparing the second measured data $S_{meas}$ and the theoretical optical response $S_{theor}$ in a fitting procedure, and determining the one or more parameters of the patterned structure from the theoretical optical response $S_{theor}$ corresponding to a best fit condition between the second measured data and the theoretical optical response.

* * * * *

UNITED STATES PATENT AND TRADEMARK OFFICE
CERTIFICATE OF CORRECTION

| | |
|---|---|
| PATENT NO. | : 10,274,435 B2 |
| APPLICATION NO. | : 15/523896 |
| DATED | : April 30, 2019 |
| INVENTOR(S) | : Boris Levant et al. |

It is certified that error appears in the above-identified patent and that said Letters Patent is hereby corrected as shown below:

In the Claims

Claim 14, Column 12, Line 16, cancel the text "input data which comprises".

Signed and Sealed this
Seventeenth Day of March, 2020

Andrei Iancu
*Director of the United States Patent and Trademark Office*